(12) United States Patent
Dooley et al.

(10) Patent No.: US 7,926,709 B1
(45) Date of Patent: *Apr. 19, 2011

(54) SYSTEMS AND METHODS FOR PHARMACY REIMBURSEMENT CLAIM RESUBMISSION

(75) Inventors: Cherie M. Dooley, Conyers, GA (US); Rita S. Russell, Atlanta, GA (US)

(73) Assignee: Per-Se Technologies, Atlanta, GA (US)

( * ) Notice: Subject to any disclaimer, the term of this patent is extended or adjusted under 35 U.S.C. 154(b) by 205 days.

This patent is subject to a terminal disclaimer.

(21) Appl. No.: 12/210,001

(22) Filed: Sep. 12, 2008

Related U.S. Application Data

(63) Continuation of application No. 11/364,987, filed on Feb. 28, 2006, now Pat. No. 7,438,218.

(60) Provisional application No. 60/657,109, filed on Feb. 28, 2005.

(51) Int. Cl.
 *G06K 15/00* (2006.01)
(52) U.S. Cl. ........................................................ 235/378
(58) Field of Classification Search .................. 235/378, 235/382.5, 383, 385; 705/2, 4
 See application file for complete search history.

(56) References Cited

U.S. PATENT DOCUMENTS

| | | | |
|---|---|---|---|
| 4,667,292 A | 5/1987 | Mohlenbrock et al. |
| 4,858,121 A | 8/1989 | Barber et al. |
| 5,550,734 A | 8/1996 | Tarter et al. |
| 5,628,530 A | 5/1997 | Thornton |
| 5,644,778 A | 7/1997 | Burks et al. |
| 5,704,044 A | 12/1997 | Tarter et al. |
| 6,012,035 A | 1/2000 | Freeman et al. |
| 6,341,265 B1 | 1/2002 | Provost et al. |
| 6,453,297 B1 | 9/2002 | Burks et al. |
| 6,757,898 B1 | 6/2004 | Ilsen et al. |
| 6,769,228 B1 | 8/2004 | Mahar |
| 6,842,736 B1 | 1/2005 | Brzozowski |
| 7,155,397 B2 | 12/2006 | Alexander et al. |
| 7,380,707 B1 | 6/2008 | Fredman |
| 2002/0002495 A1 | 1/2002 | Ullman |

(Continued)

FOREIGN PATENT DOCUMENTS

CA 2482370 A1 3/2006

(Continued)

OTHER PUBLICATIONS

Sampson, R.J., Taking Control of Health Care Costs, Best's Review—Life Health Insurance Edition, Nov. 1983, pp. 64-66, vol. 84, Issue 7, USA.

(Continued)

*Primary Examiner* — Seung H Lee
(74) *Attorney, Agent, or Firm* — Sutherland Asbill & Brennan LLP

(57) ABSTRACT

Systems, and methods for reimbursing prescription fulfillment that includes identifying a drug associated with a claim submitted by a pharmacy for reimbursement by a payer (e.g., insurance carrier) and identifying a change in a manufacturer set price associated with the drug. The invention includes monitoring reimbursed claims received from at least one payer, where one of the reimbursed claims received from the payer is associated with the drug and determining if the payer has updated its internal pricing value associated with the drug. The invention further includes generating a report that includes the payer's updated internal pricing value associated with the drug, and/or creating and submitting a reversal transaction to the at least one payer followed by a resubmission of the original claim, where the resubmitted claim value is based on the payer's updated internal pricing value associated with the drug.

37 Claims, 5 Drawing Sheets

U.S. PATENT DOCUMENTS

| | | |
|---|---|---|
| 2002/0007290 A1 | 1/2002 | Gottlieb |
| 2002/0032582 A1 | 3/2002 | Feeney, Jr. et al. |
| 2002/0042726 A1 | 4/2002 | Mayaud |
| 2002/0087583 A1 | 7/2002 | Morgan et al. |
| 2002/0111832 A1 | 8/2002 | Judge |
| 2002/0123907 A1 | 9/2002 | Strayer |
| 2002/0198831 A1 | 12/2002 | Patricelli et al. |
| 2003/0009367 A1 | 1/2003 | Morrison |
| 2003/0050799 A1 | 3/2003 | Jay et al. |
| 2003/0069760 A1 | 4/2003 | Geiber |
| 2003/0074225 A1 | 4/2003 | Borsand et al. |
| 2003/0130868 A1 | 7/2003 | Coelho |
| 2003/0149625 A1 | 8/2003 | Leonardi et al. |
| 2003/0154163 A1 | 8/2003 | Phillips et al. |
| 2003/0187695 A1 | 10/2003 | Drennan |
| 2003/0229519 A1 | 12/2003 | Eidex et al. |
| 2003/0229540 A1 | 12/2003 | Algiene |
| 2004/0039599 A1 | 2/2004 | Fralic |
| 2004/0073457 A1 | 4/2004 | Kalies |
| 2004/0078234 A1 | 4/2004 | Tallal, Jr. |
| 2004/0117323 A1 | 6/2004 | Mindala |
| 2004/0133452 A1 | 7/2004 | Denny, Jr. |
| 2004/0138921 A1 | 7/2004 | Broussard et al. |
| 2004/0148198 A1 | 7/2004 | Kalies |
| 2004/0205664 A1 | 10/2004 | Prendergast |
| 2004/0249745 A1 | 12/2004 | Baaren |
| 2005/0010446 A1 | 1/2005 | Lash et al. |
| 2005/0015280 A1 | 1/2005 | Gabel et al. |
| 2005/0060201 A1 | 3/2005 | Connely, III et al. |
| 2005/0102169 A1 | 5/2005 | Wilson |
| 2005/0154627 A1 | 7/2005 | Zuzek et al. |
| 2005/0187793 A1 | 8/2005 | Myles |
| 2005/0197862 A1 | 9/2005 | Paterson et al. |
| 2005/0240473 A1 | 10/2005 | Ayers, Jr. et al. |
| 2005/0288972 A1 | 12/2005 | Marvin et al. |
| 2006/0020514 A1 | 1/2006 | Yered |
| 2006/0026041 A1 | 2/2006 | Ullman |
| 2006/0149784 A1 | 7/2006 | Tholl et al. |
| 2006/0184391 A1 | 8/2006 | Barre et al. |
| 2006/0259363 A1 | 11/2006 | Jhetam et al. |
| 2007/0005402 A1 | 1/2007 | Kennedy et al. |
| 2007/0050209 A1 | 3/2007 | Yered |
| 2007/0136100 A1 | 6/2007 | Daugherty et al. |
| 2007/0233525 A1 | 10/2007 | Boyle |
| 2007/0233526 A1 | 10/2007 | Hoffman et al. |
| 2007/0239493 A1 | 10/2007 | Sweetland et al. |

FOREIGN PATENT DOCUMENTS

| | | |
|---|---|---|
| WO | WO 9503569 A3 | 2/1995 |
| WO | WO 0039737 A1 | 7/2000 |
| WO | WO 2007025295 A2 | 3/2007 |

OTHER PUBLICATIONS

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-PRESCRIPTIONS, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic; On-line Goes In-House, Chain Store Age Executive, Jan. 1987, pp. 128-132. vol. 63, Issue 1, USA.

Anonymous, TechRx Announces Successful Beta Deployment of T-Rex. PR Newswire. May 13, 2002.

Letter addressed to Scott Mackenzie of Per-Se Technologies from Mack Ed Swindle, Esq. of Whitaker, Chalk, Swindle & Sawyer, LLP dated Jul. 21, 2006, regarding U.S. Appl. No. 10/133,001 and U.S. Appl. No. 10/439,422.

Letter addressed to Griff Griffin, Esq. of Sutherland Asbill and Brennan LLP from Mack Ed Swindle of Whitaker, Chalk, Swindle & Sawyer, LLP dated Oct. 2, 2006 (2 pages); and attached press release dated 2001 and 2002 (2 pages), regarding U.S. Appl. No. 10/133,001 and U.S. Appl. No. 10/439,422.

Letter addressed to Christopher J. Chan, Esq. of Sutherland Asbill & Brennan LLP from Mac Ed Swindle of Whitaker, Chalk, Swindle & Sawyer, LLP dated May 8, 2007 (1 page); and attached Affidavit of Ben Loy (10 pages) regarding U.S. Appl. No. 10/133,001.

Exhibit A ("Public-Key Cryptography, NIST Special Publication 800-2," Apr. 1991) to Letter addressed to Christopher J. Chan of Sutherland Asbill & Brennan LLP from Mack Ed Swindle of Whitaker, Chalk, Swindle & Sawyer, LLP dated May 8, 2007, regarding U.S. Appl. No. 10/133,001 (132 pages).

Exhibit B ("Escrowed Encryption Standard (EES)," Feb. 9, 1994) to Letter to Christopher J. Chan of Sutherland Asbill & Brennan LLP from Mack Ed Swindle of Whitaker, Chalk, Swindle & Sawyer, LLP dated May 8, 2007, regarding U.S. Appl. No. 10/133,001 (8 pages).

Exhibit C ("Entity Authentication Using Public Key Cryptography," Feb. 18, 1997) to Letter to Christopher J. Chan of Sutherland Asbill & Brennan LLP from Mack Ed Swindle of Whitaker, Chalk, Swindle & Sawyer, LLP dated May 8, 2007, regarding U.S. Appl. No. 10/133,001 (50 pages).

Exhibit D ("Internet x. 509 Public Key Infrastructure Certificate Management Protocols," Mar. 1999) to Letter to Christopher J. Chan of Sutherland Asbill & Brennan LLP from Mack Ed Swindle of Whitaker, Chalk, Swindle & Sawyer, LLP dated May 8, 2007, regarding U.S. Appl. No. 10/133,001 (65 pages).

Exhibit E ("PDX 4.0 Pharmacy Manual, Canada Claims section from Jan. 2000," Feb. 18, 1997) to Letter to Christopher J. Chan of Sutherland Asbill & Brennan LLP from Mack Ed Swindle of Whitaker, Chalk, Swindle & Sawyer, LLP dated May 8, 2007, regarding U.S. Appl. No. 10/133,001 (4 pages).

Letter addressed to Mac Ed Swindle of Whitaker, Chalk, Swindle & Sawyer, LLP from Christopher J. Chan, Esq. of Sutherland Asbill & Brennan LLP dated May 30, 2007, regarding U.S. Appl. No. 10/133,001 (2 pages).

Letter addressed to Christopher J. Chan, Esq. of Sutherland Asbill & Brennan LLP from Mac Ed Swindle of Whitaker, Chalk, Swindle & Sawyer, LLP dated May 15, 2007 (1 page) regarding U.S. Appl. No. 11/364,987 (3 pages) and referenced attachments (OPUS-ISM LLC web page—1 page) and (CareMax Connection brochure excerpt—2 pages).

Letter addressed to Mac Ed Swindle of Whitaker, Chalk, Swindle & Sawyer, LLP from Christopher J. Chan, Esq. of Sutherland Asbill & Brennan LLP dated Jun. 7, 2007, regarding U.S. Appl. No. 11/364,987 (2 pages).

Letter addressed to Mac Ed Swindle of Whitaker, Chalk, Swindle & Sawyer, LLP from Griff Griffin, Esq. of Sutherland Asbill & Brennan LLP dated Sep. 14, 2006, regarding U.S. Appl. No. 10/439,422 (2 pages).

Letter addressed to Christopher J. Chan, Esq. of Sutherland Asbill & Brennan LLP from Mac Ed Swindle of Whitaker, Chalk, Swindle & Sawyer, LLP dated May 8, 2007, regarding U.S. Appl. No. 10/439,422 (1 page).

Affidavit of Ken Hill to letter addressed to Christopher J. Chan, Esq. of Sutherland Asbill & Brennan LLP from Mac Ed Swindle of Whitaker, Chalk, Swindle & Sawyer, LLP dated May 8, 2007, regarding U.S. Appl. No. 10/439,422 (5 page) and attached Exhibits A (5 pages) and B (49 pages).

Letter addressed to Mac Ed Swindle of Whitaker, Chalk, Swindle & Sawyer, LLP from Christopher J. Chan, Esq. of Sutherland Asbill & Brennan LLP dated Jun. 7, 2007, regarding U.S. Appl. No. 10/439,422 (2 pages).

Issue Notification for U.S. Appl. No. 11/364,987.

Notice of Allowance for U.S. Appl. No. 11/364,987.

AWP Resubmission

AWP Resubmission — 302

AWP Resubmission     AWP Resubmit
Detail

Report Help
Export this page
Printer-Friendly Format
Open Floating Headers

Report Includes:
   Date Range: February 13-19, 2005

Report Excludes:
   No Exclusions

RESET REPORT

Number of rows Displayed: 11 out of 11

| Store ID Hide | Rx Number Hide | Rx Fill Date Hide | AWP Eff Date Hide | BIN Hide | BIN Description Hide | NDC Hide | Drug Name Hide | AWP Per Unit Before Hide | AWP Per Unit After Hide | Orig Ingred Cost Paid Hide | %Off New AWP Hide | %Off Old AWP Hide | Patient Pay Hide | Potential Opportunity Hide | Opportunity Date Hide |
|---|---|---|---|---|---|---|---|---|---|---|---|---|---|---|---|
| 1998 | 3623550 | 08-02-05 | 2005-01-13 | 410016 | NDC Healthcare | 60598-0003-01 | NIASPAN 1,000 MG TABLET SA | $2.43 | $2.66 | $126.34 | 13.58% | 21.00% | $15.00 | $35.53 | 13-02-05 |
| 1998 | 3622501 | 29-01-05 | 2005-01-17 | 410016 | NDC Healthcare | 50474-0592-40 | KEPPRA 500 MG TABLET | $2.33 | $2.58 | $43.87 | 21.00% | 28.46% | $20.00 | $103.87 | 15-02-05 |
| 1998 | 3627782 | 09-02-05 | 2005-02-01 | 410016 | NDC Healthcare | 00074-3290-13 | TARKA 4/240 MG TABLET SA | $2.16 | $2.25 | $37.29 | 17.92% | 21.00% | $3.00 | $6.23 | 18-02-05 |
| 1998 | 3637340 | 09-02-05 | 2005-02-01 | 410016 | NDC Healthcare | 00074-3290-13 | TARKA 4/240 MG TABLET SA | $2.16 | $2.25 | $121.63 | 17.92% | 21.00% | $3.00 | $6.23 | 18-02-05 |

| Store Id | Rx Nbr | Rx Fill Date | AWP Eff Date | BIN | BIN Desc | PCN | % off Old AWP | % off New AWP | Potential Oppt | Orig Ing Cost Paid | Patient Pay $ | NDC | Drug Name | Qty Disp |
|---|---|---|---|---|---|---|---|---|---|---|---|---|---|---|
| 9906279 | 6783949 | 8/1/05 | 7/29/05 | 00232 | NDC MEDICAL | TZS | 0.12999 | 0.15532 | 11.20 | 373.63 | 40.00 | 99207049250 | DYNACIN 100 MG TABLET | 60.000 |
| 9946809 | 6835927 | 8/1/05 | 7/29/05 | 00232 | NDC MEDICAL | TZS | 0.12999 | 0.15532 | 11.20 | 373.63 | 40.00 | 99207049250 | DYNACIN 100 MG TABLET | 60.000 |
| 9924189 | 6652065 | 8/1/05 | 7/29/05 | 616616 | NDC PRESCRIPTIONS | TZS | 0.12999 | 0.15532 | 11.20 | 373.63 | 40.00 | 99207049250 | DYNACIN 100 MG TABLET | 60.000 |
| 9925709 | 6656135 | 8/1/05 | 7/29/05 | 616616 | NDC PRESCRIPTIONS | TZS | 0.12999 | 0.15532 | 11.20 | 373.63 | 40.00 | 99207049250 | DYNACIN 100 MG TABLET | 60.000 |
| 9939049 | 6818896 | 8/1/05 | 7/29/05 | 007777 | NDC SCRIBERS | TZS | 0.12999 | 0.15532 | 11.20 | 373.63 | 40.00 | 99207049250 | DYNACIN 100 MG TABLET | 60.000 |
| 9950379 | 6985392 | 8/1/05 | 7/29/05 | 007777 | NDC SCIRBERS | TZS | 0.12999 | 0.15532 | 11.20 | 373.63 | 40.00 | 99207049250 | DYNACIN 100 MG TABLET | 60.000 |
| 9917199 | 6689409 | 8/1/05 | 7/29/05 | 012345 | NDC V3 | TZS | 0.12999 | 0.15532 | 11.20 | 373.63 | 40.00 | 99207049250 | DYNACIN 100 MG TABLET | 60.000 |
| 992589 | 6614674 | 8/1/05 | 7/29/05 | 012345 | NDC V3 | TZS | 0.12999 | 0.15532 | 11.20 | 373.63 | 40.00 | 99207049250 | DYNACIN 100 MG TABLET | 60.000 |
| 9917199 | 6687387 | 8/1/05 | 7/29/05 | 009999 | NDC THERAPEUTICS | TZS | 0.12999 | 0.15532 | 11.20 | 373.63 | 40.00 | 99207049250 | DYNACIN 100 MG TABLET | 60.000 |
| 9936489 | 6763570 | 8/1/05 | 7/29/05 | 009999 | NDC THERAPEUTICS | TZS | 0.12999 | 0.15532 | 11.20 | 373.63 | 40.00 | 99207049250 | DYNACIN 100 MG TABLET | 60.000 |
| 9921384 | 6783952 | 8/1/05 | 7/29/05 | 987654 | NDC SOLUTIONS | TZS | 0.12999 | 0.15532 | 11.20 | 373.63 | 40.00 | 99207049250 | DYNACIN 100 MG TABLET | 60.000 |
| 9960124 | 6835912 | 8/1/05 | 7/29/05 | 987654 | NDC SOLUTIONS | TZS | 0.12999 | 0.15532 | 11.20 | 373.63 | 40.00 | 99207049250 | DYNACIN 100 MG TABLET | 60.000 |
| 9910436 | 6652096 | 8/1/05 | 7/29/05 | 008888 | NDC (GA) V2 | TZS | 0.12999 | 0.15532 | 11.20 | 373.63 | 40.00 | 99207049250 | DYNACIN 100 MG TABLET | 60.000 |
| 9998745 | 6818803 | 8/1/05 | 7/29/05 | 555555 | NDC CARE | TZS | 0.12999 | 0.15532 | 11.20 | 373.63 | 40.00 | 99207049250 | DYNACIN 100 MG TABLET | 60.000 |
| 9942190 | 6678333 | 8/1/05 | 7/29/05 | 001111 | NDC HEALTH SYS | TZS | 0.12999 | 0.15532 | 11.20 | 373.63 | 40.00 | 99207049250 | DYNACIN 100 MG TABLET | 60.000 |
| 9980376 | 6763549 | 8/1/05 | 7/29/05 | 333333 | NDC HEALTHCARE | TZS | 0.12999 | 0.15532 | 11.20 | 373.63 | 40.00 | 99207049250 | DYNACIN 100 MG TABLET | 60.000 |

Activity Summary

Current View | Pending View | Resubmission Summary | Summary View | Activity Summary | Audit Log | BIN Exclusion Log | NDC Exclusion Log AWP Resubmission Change Password | Logout | Help | User Profile Date Range – From: 2/20/2005  To: 2/20/2005  [Load] [Download]
Sort By: [Ascending] [Go]

| Service Date | Rx Nbr | Store ID | Date Processed | Reversal Status | Billing Status | BIN | NDC | Drug Name | Orig Ing Cost Paid | New Ing Cost Sub | New Ing Cost Paid | Increased Reimbursement | Reject Code 1 | Reject Code 2 |
|---|---|---|---|---|---|---|---|---|---|---|---|---|---|---|
| 2/17/2005 | 6789349 | 9906179 | 2/20/2005 | A | P | 730408 | 00051845030 | ANDROGEL 1% (50MG) GEL PCKT | 360.68 | 440.40 | 378.74 | 18.06 | | |
| 2/8/2005 | 6835927 | 9946809 | 2/20/2005 | A | P | 004122 | 00023918707 | LUMIGAN 0.03% EYE DROPS | 162.54 | 199.33 | 173.92 | 11.38 | | |
| 2/14/2005 | 6652065 | 9924189 | 2/20/2005 | A | P | 004122 | 00023918707 | LUMIGAN 0.03% EYE DROPS | 162.54 | 199.33 | 173.92 | 11.38 | | |
| 2/15/2005 | 6656135 | 9925709 | 2/20/2005 | A | P | 730408 | 00051845030 | ANDROGEL 1% (50MG) GEL PCKT | 180.34 | 220.20 | 189.37 | 9.03 | | |
| 2/9/2005 | 8818896 | 9939049 | 2/20/2005 | A | P | 390123 | 99207001301 | LOPROX 0.77% GEL | 143.65 | 177.05 | 152.26 | 8.61 | | |
| 1/21/2005 | 6985392 | 9950379 | 2/20/2005 | A | C | 004122 | 0006380109 | MAXALT MLT 10 MG TABLET | 246.05 | 291.80 | 254.60 | 8.55 | | |
| 1/24/2005 | 6689409 | 9917799 | 2/20/2005 | A | C | 004122 | 0006380109 | MAXALT MLT 10 MG TABLET | 196.84 | 233.44 | 203.68 | 6.84 | | |
| 2/16/2005 | 6124938 | 9967125 | 2/20/2005 | A | P | 730408 | 44087081808 | CRINONE 8% GEL | 92.00 | 113.40 | 98.66 | 6.44 | | |
| 2/10/2005 | 4964177 | 8924653 | 2/20/2005 | A | P | 730408 | 00023917705 | ALPHAGAN D 0.15% EYE DROPS | 113.55 | 138.63 | 119.22 | 5.67 | | |

Page 1 of 7 (64 Records)

First Page | Prev Page | Next Page

Summary:
Total Claims: 64
Total Increased Reimbursement: 243.60
Total Rejections: 1
Percentage Rejections: 1.56
Reversal Rejections: 0
Percentage Reversal Rejections: 0
Resubmission Rejections: 1
Percentage Resubmission Rejections: 1.56
Resubmission Rejections Original Paid: 83.90

FIG. 5

SYSTEMS AND METHODS FOR PHARMACY REIMBURSEMENT CLAIM RESUBMISSION

RELATED APPLICATION

This application claims the benefit of priority to U.S. patent application Ser. No. 11/364,987, entitled "Systems and Methods for Pharmacy Reimbursement Claim Resubmission" filed in the United States Patent and Trademark Office on Feb. 28, 2006, which in turn claims the benefit of priority to U.S. Provisional Patent Application Ser. No. 60/657,109, entitled "AWP Resubmission System and Methods," which was filed in the United States Patent and Trademark Office on Feb. 28, 2005, both of which are incorporated by reference herein.

FIELD OF THE INVENTION

This invention relates to the submission and reimbursement of insurance claims. More specifically, it relates to the submission and reimbursement monitoring of insurance claims in the pharmaceutical industry for prescription fulfillment.

BACKGROUND OF THE INVENTION

In the pharmaceutical industry, drug manufacturers often establish what is known as a Average Wholesale Price ("AWP"), or AWP, for individual products (e.g., drugs). The AWP is the price assigned to a drug (e.g., brand name or generic) and is currently listed in the Red Book, First DataBank and/or Medispan, which are data source providers that provide drug information related services and monitor current drug information. AWP is a commonly used price index in pharmaceutical transactions. State Medicaid Agencies use AWP to calculate payments to retail pharmacies for providing drug products to Medicaid patients. Prescription benefit managers (PBMs), insurance carriers (which may include a group of insurance carriers, referred to by a Bank Identification Number or "BIN," administering claims on behalf of one or more insurance carriers), and managed care organizations (MCOs) use the AWP for a particular drug to determine the appropriate reimbursement amount to pay a retail pharmacy who fills their customer's prescriptions for that particular drug. Pharmacies often use AWP as a cost basis for pricing their prescriptions to patients, such pricing of a drug by an individual pharmacy is referred to as the Usual and Customary ("U & C") price, retail or "cash" price. AWP is not required to reflect the price of any actual sale of drugs by a manufacturer, nor is it defined in law. Rather, drug manufacturers adjust their AWPs fairly often depending on a variety of factors both business related and market related.

Often there is a lag in time between when the drug manufacturers make their adjustments to the AWP for a particular drug and when the insurance processors adjust the AWP values they each use to determine an appropriate reimbursement for that particular drug. As a result, a pharmacy may end up paying a higher purchase price for a particular dug than what they would be reimbursed for by an insurance processor. For example, drug X has an AWP of $5 a pill on January $1^{st}$. Drug X's manufacturer increases the AWP of that particular drug on January $15^{th}$ to $10 a pill. Insurance processor Y updates its AWP databases only on the first of every month. Therefore, a pharmacy submitting a reimbursement claim to insurance processor Y on January $20^{th}$ will be reimbursed at the $5 a pill rate and not the $10 a pill current market rate.

Such use of outdated pricing values in claim reimbursement may prove costly to pharmacies. Further, delaying claim submissions or dedicating resources for pharmacies to individually monitor their payer's use of pricing values requires unnecessary cost and labor to pharmacies as well. Therefore, what is needed are systems and methods that address these problems of current claim reimbursement systems.

SUMMARY OF THE INVENTION

According to an embodiment of the invention, there is disclosed a method for reimbursing prescription fulfillment that includes identifying a change in a manufacturer set price associated with the drug; monitoring one or more adjudicated claims received from a payer, where at least one of the adjudicated claims received from the payer is associated with a drug. The method further includes determining if the payer has updated an internal pricing value associated with the drug; and generating a report, where the report includes a potential reimbursement value associated with the drug based on the determination of an updated internal pricing value associated with the drug.

According to one aspect of the invention, the method may further include storing the claim submitted for reimbursement in a database. In accordance with another aspect of the invention, the method may further include scrubbing one or more adjudicated claims received from at least one payer. According to yet another aspect of the invention, the method may further include providing access to claim information through a user interface. In accordance with yet another aspect of the invention, the method may further include transmitting the report to one or more users. According to another aspect of the invention, the determination of when the payer has updated an internal pricing value associated with the drug may include reviewing a first reimbursement value associated with a first adjudicated reimbursement claim submitted to the payer; and comparing the first reimbursement value to a second reimbursement value associated with a second adjudicated claim submitted to the same payer. In accordance with yet another aspect of the invention, the identification of a change in the manufacturer set price associated with the drug may include receiving an indication of the change in the manufacturer set price of the drug from a monitoring service.

According to another embodiment of the invention, there is disclosed a method for reimbursing prescription fulfillment that includes identifying a change in an average wholesale price (AWP) associated with a drug; and monitoring one or more adjudicated claims received from a payer, where at least one of the adjudicated claims received from the payer is associated with the drug. The method further includes determining if the payer has updated an internal AWP value associated with the drug; upon receiving a request from a user, creating a reversal transaction of at least one adjudicated claim associated with the drug; and then submitting the reversal transaction to one or more payers.

In accordance with one aspect of the invention, the method further includes that upon acceptance of the reversal transaction by the payer, resubmitting at least one adjudicated claim. According to another aspect of the invention, the method further includes a transaction file, where the transaction file includes data associated with the claim that is being reversed and/or resubmitted to a payer. In accordance with yet another aspect of the invention, the method further includes providing access to the transaction file through a user interface. According to yet another aspect of the invention, the method further includes transmitting the transaction file to a user. In accordance with yet another aspect of the invention, the method further includes scrubbing one or more adjudicated claims received from at least one payer.

According to yet another embodiment of the invention, there is disclosed a system for submitting prescription reimbursement claims that includes one or more pharmacy point-of-service (POS) devices and a host server in communication with both pharmacy POS devices and one or more payer systems through a network. The host server includes a processor that executes software instructions for identifying a change in an average wholesale price (AWP) associated with the drug, monitoring one or more adjudicated claims received from a payer, where at least one of the adjudicated claims received from the payer is associated with the drug, and determining if the payer has updated an internal AWP value associated with the drug.

According to one aspect of the invention, the processor of the host server of the system further executes software instructions for generating a report, where the report includes a potential reimbursement value associated with the drug based on the determination of an updated internal pricing value associated with the drug. In accordance with another aspect of the invention, the processor of the host server of the system further executes software instructions for scrubbing one or more adjudicated claims received from at least one payer. According to yet another aspect of the invention, the processor of the host server of the system further executes software instructions for creating a reversal transaction based on at least one adjudicated claim associated with the drug; and submitting the reversal transaction to the payer. In accordance with yet another aspect of the invention, the processor of the host server of the system further executes software instructions for, upon acceptance of the reversal transaction by the payer, resubmitting at least one adjudicated claim. According to another aspect of the invention, the processor of the host server of the system further executes software instructions for creating a transaction file, where the transaction file includes data associated with the one or more resubmitted claims. In accordance with yet another aspect of the invention, the system further includes a user interface provided by the host sever and accessible through the internet.

BRIEF DESCRIPTION OF THE FIGURES

Figure 1:
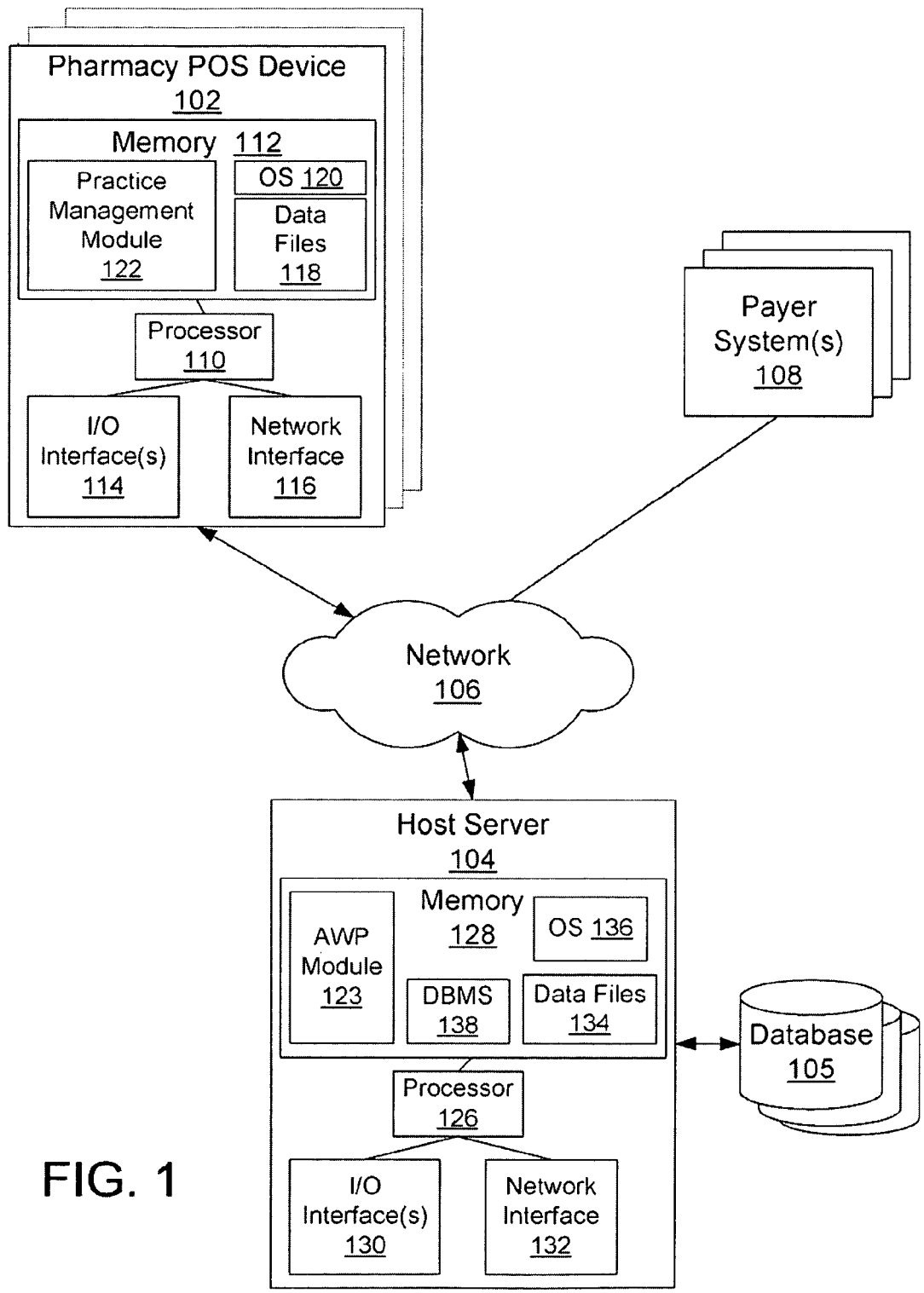

Having thus described the invention in general terms, reference will now be made to the accompanying drawings, which are not necessarily drawn to scale, and wherein:

FIG. 1 shows a claim resubmission processing system according to one aspect of the present invention.

Figure 2:
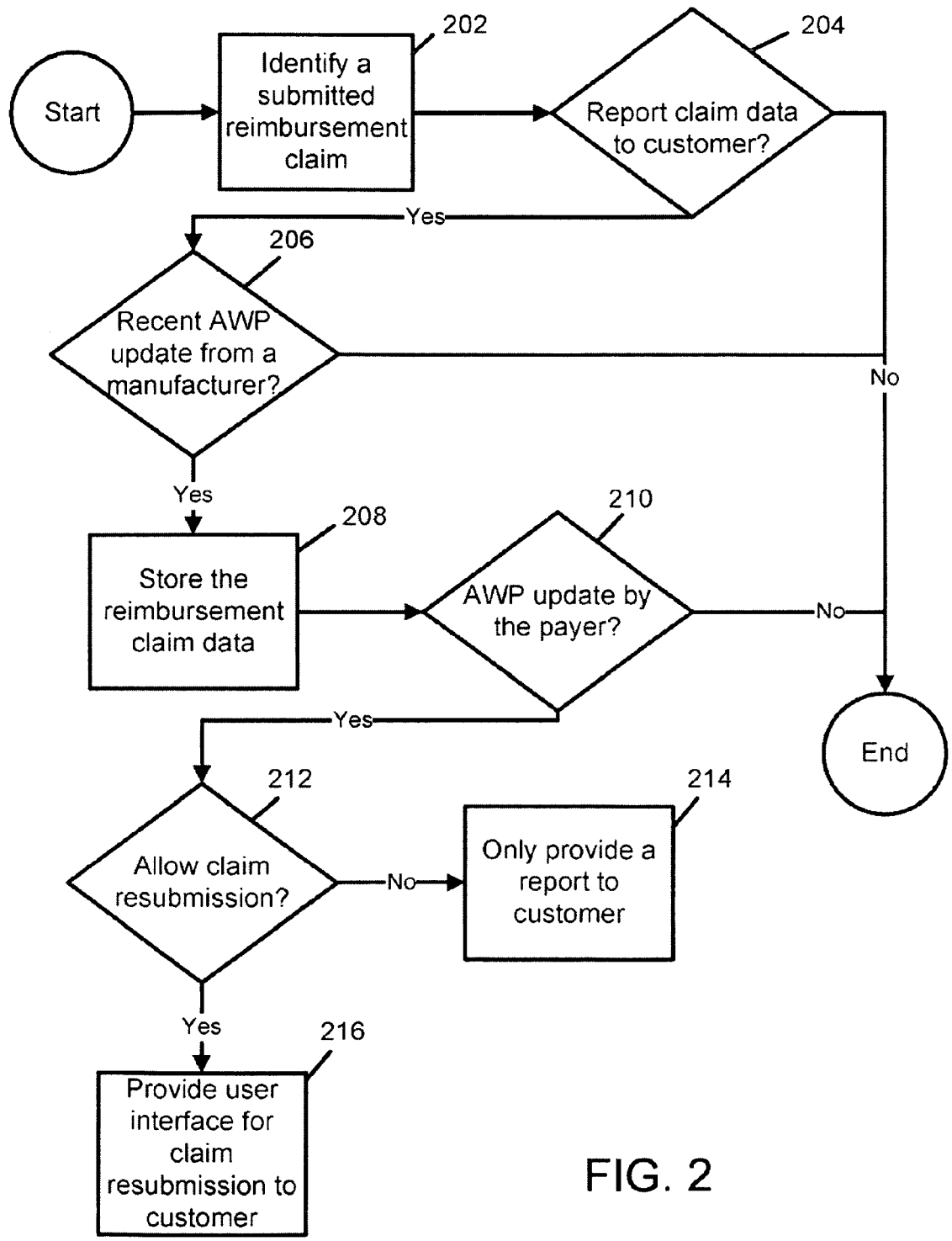

FIG. 2 shows a block diagram flowchart showing the process of monitoring and reporting the changes in drug pricing by a payer system according to one embodiment of the present invention.

FIG. 3 shows an exemplary report generated to summarize a customer's reversal/resubmission opportunities according to one embodiment of the present invention.

FIG. 4 shows an exemplary user interface screen offering user options to initiate claim reversal and resubmission according to one embodiment of the present invention.

FIG. 5 shows an exemplary transaction file accessed through the user interface summarizing resubmitted claim activity according to one embodiment of the present invention.

DETAILED DESCRIPTION OF THE INVENTION

The present invention is directed to resubmission systems and methods that assist pharmacies in maximizing their reimbursement from one or more insurance processors for filling a prescription of one of their customers. The resubmission systems and methods of the present invention enable a user to reverse and/or resubmit transactions when a price increase has been indicated by a manufacturer and the claim was paid using an old price value in the reimbursement calculation. In an exemplary embodiment of the invention, the resubmission system provides a pharmacy the option of resubmitting a reimbursement claim once the insurance processor has updated its internal price to reflect the manufacturers updated price. Thus, the pharmacy receives the most recently, updated price set by the manufacturer for the particular drug in the reimbursement claim. The resubmission systems and methods of the present invention may improve the productivity of resources required to monitor, correct, and resubmit claims for updated pricing as well as improve the cash flow and profit margins of pharmacies by ensuring the most-up-to-date pricing of transactions. The resubmission systems and methods of the present invention may be utilized by retail pharmacies (chains, regional pharmacies, independent pharmacies, etc.), mass merchandisers pharmacies, various food and drug industry segments pharmacies, mail order entities, LTC entities, as well as others. Such entities may be referred to throughout this description as "customers."

For the purposes of providing an exemplary embodiment of the invention only, the systems and methods described below will be in reference to manufacturer established Average Wholesale Price ("AWP") values, as that is the current form of drug pricing (e.g., manufacturer(s) set price) used by payer systems to price pharmacy reimbursement claims. In alternative embodiments of the present invention, the claim submission system and methods discussed below may be modified to operate the same functions and processes based on monitoring pricing elements similar to AWP that may be used in the future to price pharmacy reimbursement claims in addition to or in place of the AWP values. For example, the claim submission system and methods discussed below may be modified to operate the same functions and processes based on monitoring Wholesale Acquisition Cost ("WAC"), which is also set by the manufacturer(s), Maximum Allowable Cost ("MAC"), which may vary from payer to payer or other pricing schemes similar to the use of an AWP. Other examples may include if a government agency or third party entity were to periodically update the pricing of drugs for reimbursement of prescription fulfillment claims, rather than manufacturers establishing an AWP value associated with a particular drug, or if a manufacturer (or group of manufacturers) changed their pricing schemes from being AWP based to some other value and/or calculation based pricing scheme, then the claim submission system and methods of the invention may be modified to identify such updates in drug pricing and determine when payers have updated their internal pricing to reflect such updates in drug prices in order to maximize reimbursements of claims submitted from pharmacies to those payers through the claim reversal and/or resubmission methods described below.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

The present invention is described below with reference to block diagrams and flowchart illustrations of systems, methods, apparatuses and computer program products according to an embodiment of the invention. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means that implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Exemplary embodiments of the present invention will hereinafter be described with reference to the figures, in which like numerals indicate like elements throughout the several drawings. FIG. 1 shows a block diagram claim processing system according to one aspect of the present invention. In particular, FIG. 1 is an exemplary operating environment for implementation of certain embodiments of the present invention, including a pharmacy point-of-service ("POS") device 102, a host server 104 and a payer system 108, which are each configured for accessing and reading associated computer-readable media having stored thereon data and/or computer-executable instructions for implementing the various methods of the present invention. Generally, network devices and systems include hardware and/or software for transmitting and receiving data and/or computer-executable instructions over a communications link and a memory for storing data and/or computer-executable instructions. Network devices and systems may also include a processor for processing data and executing computer-executable instructions, as well as other internal and peripheral components that are well known in the art. As used herein, the term "computer-readable medium" describes any form of memory or a propagated signal transmission medium. Propagated signals representing data and computer-executable instructions are transferred between network devices and systems.

As shown in FIG. 1, a pharmacy POS device 102 may be in communication with the host server 104 via a network 106. The pharmacy POS device 102 may be configured for receiving prescription claim data, creating claim reimbursement transactions therefrom and transmitting said claim reimbursement transactions to the host server 104. Prescription claim data includes any data that is typically provided by a patient, pharmacist and/or other health care provider in relation to filling a prescription (e.g., cost associated with filling the prescription, etc.) and/or requesting approval or authorization for payment from a payer or claim adjudicator. A payer may be an insurance company, a financial institution or another financial service provider. Prescription claim data may be input to the pharmacy POS device 102 by a pharmacist or other health care provider or may be received by the pharmacy POS device 102 in electronic form from an electronic prescription service (not shown). The pharmacy POS device 102 may be configured for handling other types of prescription transactions.

Prescription claim transactions are electronic records or messages intended to facilitate the communication of prescription information. For example, prescription claim transactions are intended to communicate prescription claim data between pharmacies (i.e., providers) and payers. Although prescription claim transactions will be discussed hereinafter, it should be understood that the various systems and methods of the invention may be practiced in connection with other types of prescription transactions or independently of prescription transactions (e.g., raw prescription data). The content and format of a prescription claim may vary depending on which standard or protocol is used. In general, however, prescription claim transactions will identify the intended payer recipient, the drug product to be dispensed or previously dispensed, e.g., by National Drug Code number ("NDC"), the quantity to be dispensed as well as the days supply, whether the prescription claim relates to a new prescription or a refill prescription, and billing-related information.

Prescription claim transactions may be transmitted from the pharmacy POS device 102 to the host server 104 in batch, real-time or near real-time. Pharmacy POS devices can connect to the host server 104 through a variety of methods, including dial-up, frame relay or leased-line. The entire system is preferably supported by redundant software, communications links, and uninterruptible power supplies, thereby ensuring that all connections will provide reliable, continuous operation. The system also preferably ensures that all of provider-submitted claims transactions are routed quickly, accurately, and consistently. The claim processing system substantially reduces the costs of submitting claims and speeds up providers' payment cycles.

In certain embodiments, the host server 104 may serve as a clearinghouse for multiple payer systems 108. As noted above, payer systems 108 may include systems operated by insurance companies, financial institutions and other financial service providers. In its capacity as a clearinghouse, the host server 104 is operable to parse prescription claim transactions and forward them to the appropriate payer system 108 for processing. Approval, authorization or rejection messages may be returned to the host server 104 from the payer systems 108 and such messages may be forwarded by the host server 104 to the pharmacy POS device 102.

In serving as a clearinghouse, the host server 104 may also be configured for performing pre-editing and post-editing of prescription claim transactions. Pre-editing and post-editing refers to real-time or near real-time validation and management of prescription claim data in order to maximize prescription claim reimbursement and minimize claim submission errors. Pre-editing and post-editing may generate messaging alerts and/or retrospective reports supporting "usual and customary" price comparisons, average wholesale price ("AWP") edits, dispense as written ("DAW"), brand appropriateness, and numerous other screening processes for facilitating rapid and accurate validation of prescription claims.

In accordance with the present invention, the host server 104, and more particularly, the AWP module 123, may be configured for performing certain claim screening, reporting, and editing processes for the detection and correction of AWP reimbursement values in a claim reimbursement transaction, whether it be an original submission, reversal or the resubmission of a claim. An exemplary process conducted by the AWP module 123 in accordance with the invention is described in further detail below with reference to FIG. 2. A pharmacy seeking the appropriate reimbursement uses the AWP module 123 to monitor both the current AWP price established by the manufacturer and the reimbursement values paid by the insurance processors. Therefore, the AWP module 123 may comprise computer-executable instructions for performing various processes for reviewing, storing and possibly editing reimbursement claims, as well as managing related messaging and reporting functions regarding the AWP values used during the adjudication of a claim by a payer system 108. The host server 104 intercepts claims adjudicated by the payer system 108, and the AWP module 123 parses and examines the claim's contents. If instructed to do so by the user operating the pharmacy POS device 102, the AWP module 123 then determines if the claim contains the appropriate AWP value. This process will be discussed in further detail below. The AWP module 123 forwards the claim to its intended payer. However, where a claim fails to meet payer-provided claim criteria, the AWP module 123 can transmit a claim reject message to the pharmacy POS device 102, so that the pharmacy can correct the claim error and retransmit the claim. Reject messages may indicate that a prescription claim has been rejected, provide a pharmacist with information about the claim error, and may encourage the pharmacist to correct the prescription claim.

The claim criteria may also dictate actions that should be taken, such as messages transmitted to a pharmacy concerning the claim reimbursement value. The claim criteria can also instruct the module 123 that the claim should be compared against databases of objective information, such as drug lists or current AWP values provided by manufacturers or other sources, or against historical data, such as historical consumer claim information, stored in one or more databases associated with the host server 104 and described below. The submitted claim reimbursement may be corrected by the AWP module 123 and forwarded to the intended payer system 108 in an attempt to maximize the reimbursed value of the submitted claim. Finally, the AWP screening and editing processes according to the present invention may also be designed to capture certain prescription claim data (e.g., AWP pricing information) for subsequent analysis and reporting related to claim errors transmitted from pharmacy POS devices 102.

Referring again to FIG. 1, it will be appreciated that the pharmacy POS device 102 may be any processor-driven device, such as a personal computer, laptop computer, handheld computer and the like. In addition to a processor 110, the pharmacy POS device 102 may further include a memory 112, input/output ("I/O") interface(s) 114 and a network interface 116. The memory 112 may store data files 118 and various program modules, such as an operating system ("OS") 120 and a practice management module 122. The practice management module 122 may comprise computer-executable instructions for performing various routines, such as those for creating and submitting prescription claim transactions. I/O interface(s) 114 facilitate communication between the processor 110 and various I/O devices, such as a keyboard, mouse, printer, microphone, speaker, monitor, etc. The network interface 116 may take any of a number of forms, such as a network interface card, a modem, etc. These and other components of the pharmacy POS device 102 will be apparent to those of ordinary skill in the art and are therefore not discussed in more detail herein.

Similarly, the host server 104 may be any processor-driven device that is configured for receiving and fulfilling requests related to prescription claim transactions. The host server 104 may therefore include a processor 126, a memory 128, input/output ("I/O") interface(s) 130 and a network interface 132. The memory 128 may store data files 134 and various program modules, such as an operating system ("OS") 136, a database management system ("DBMS") 138 and the AWP module 123. The host server 104 may include additional program modules (not shown) for performing other pre-editing or post-editing methods and for providing clearinghouse services. Those skilled in the art will appreciate that the host server 104 may include alternate and/or additional components, hardware or software. In addition, the host server 104 may be connected to a local or wide area network (not shown) that includes other devices, such as routers, firewalls, gateways, etc.

The host server 104 may include or be in communication with one or more databases 105. The database 105 may store, for example, data relating to pharmacies, payers, state prescription laws, prescription drugs, formularies, and consumers, such as typical doses filled by consumers, typical drugs prescribed by doctors, most common daily dose values, common daily dose values, likelihood indicators and other data used in the various claim screening and editing processes described hereinafter. The database 105 may also store reports and other data relating to the results of the claim screening and edit processes. The database 105 may of course also store any other data used or generated by the host server 104 or AWP module 123, such as data used in other pre-editing and post-editing methods and reports generated thereby. Although a single database 105 is referred to herein for simplicity, those skilled in the art will appreciate that multiple physical and/or logical databases may be used to store the above mentioned data. For security, the host server 104 may have a dedicated connection to the database 105, as shown. However, the host server 104 may also communicate with the database 105 via a network 106.

The network 106 may comprise any telecommunication and/or data network, whether public or private, such as a local area network, a wide area network, an intranet, an internet and/or any combination thereof and may be wired and/or wireless. Due to network connectivity, various methodologies as described herein may be practiced in the context of distributed computing environments. Although the exemplary pharmacy POS device 102 is shown for simplicity as being in communication with the host server 104 via one intervening network 106, it is to be understood that any other network configuration is possible. For example, the pharmacy POS device 102 may be connected to a pharmacy's local or wide area network, which may include other devices, such as gateways and routers, for interfacing with another public or private network 106. Instead of or in addition to a network 106, dedicated communication links may be used to connect the various devices of the present invention.

Those skilled in the art will appreciate that the operating environment shown in and described with respect to FIG. 1 is provided by way of example only. Numerous other operating environments, system architectures and device configurations are possible. For example, the invention may in certain embodiments be implemented in a non-networked environment, in which a stand-alone pharmacy POS device 102 executes one or more AWP module(s) 123. Accordingly, the present invention should not be construed as being limited to any particular operating environment, system architecture or device configuration.

Using the claim processing system, providers can transmit in real-time provider-submitted claims to an appropriate payer and return a claim approval or rejection within seconds. Thus, the claim processing system can streamline provider claim processing operations and increase productivity for both providers and benefit plans. To enable the provider to input claims for electronic transmission to the claim processing system and payer, the pharmacy POS device 102 may comprise software that receives claim data entered by a user through a graphical user interface (GUI). According to one aspect of the invention, no claim processing software resides on the POS device 102, other than an Internet browser, because the GUI and one or more interfaces for inputting claim data are stored by the claim processing system and remotely accessible by the POS device 102 via an Internet connection, satellite or cellular network, LAN, WAN, or the like. Using the GUI information such as a patient's name, birth date, address, telephone number and other identifying information is entered with claim-specific information, such as drug prescription or medical service or procedure. The identity of the pharmacy is also included in the claim data along with additional information known to those of ordinary skill in the art.

According to one aspect of the invention the claim data fields are defined by a particular payer such that the POS device 102 should provide only the claim data requested by the payer to which the claim is transmitted. According to another aspect of the invention the claim data is defined by a pre-established standard or transaction format well known to those of skill in the art. Once the claim is entered, it is transmitted to the host server 104 via any of the methods described above. The claim is then edited by the host server 104 and/or forwarded by the host server 104 to the appropriate payer system 108. Preferably, the claim processing system, and more particularly, the host server 104, is an all-payer solution allowing providers to use a single application to connect to key government and commercial payers across the country.

FIG. 2 shows a block diagram flowchart showing the process of monitoring and reporting the changes in drug pricing by a payer system according to one embodiment of the present invention. As shown in the exemplary embodiment of FIG. 2, the process starts at step 202 where a customer's (e.g., pharmacy) initial reimbursement claim(s) having been adjudicated or paid by a payer system (e.g., insurance processor or group of insurance processors) is identified and/or captured and may be stored in an AWP evaluation table located in one or more databases associated with the AWP module.

Step 204 may be invoked to further determine if the submitted transaction should be reported to the customer (e.g., pharmacy). Step 204 "scrubs" the claim reimbursement data stored in AWP evaluation tables from previously adjudicated claim transactions. Scrubbing is a process where captured transactions may be excluded from being reported back to the customer at the pharmacy POS. For example, transactions may be "scrubbed" for BIN or NDC exclusions, same-day and prior-day reversals, paid at U & C rate, 100% co-pay and other transactions where resubmission may not be possible or desirable. For example, the process may be instructed to ignore transactions where the patient paid 100% of the bill for multiple pills where the ingredient cost paid and the total amount paid is not null, or where claims are paid at the U & C rate. In an exemplary embodiment of the invention, scrubbing is done through a batch process which is run nightly, to ensure that the scrubbing occurs to the most recent transactions. In such an embodiment, same day reversals and the originating transaction may be scrubbed as well as prior day reversals. In alternative embodiments, the scrubbing of the data stored in the AWP evaluation tables may be conducted more or less frequent and even may be conducted in real time prior to each claim submission.

In alternative embodiments of the invention, resubmission opportunities may only be presented to customers once it has been confirmed through additional calculations, monitoring of recently reimbursed claims, and/or notification from a payer or monitoring service that the payer has updated their pricing file(s) to reflect the new AWP set by the manufacturer. Various thresholds, parameters and other screening tools (adjustable by a customer, technician or other system's operator through a user interface) may be implemented to configure the detection of the AWP price change to occur only at times the customer would want to be notified. For example, a customer may instruct the system to ignore the change in a reimbursement value if the calculation detects a percentage change below (or above) a particular percentage to reflect a contracted reimbursement rate with the payer or for other reasons. This customization would allow a customer to only be notified on claims that are more likely to be reversed, are worth the time to resubmit the claim, or other reasons. In an alternative embodiment of the invention, additional adjustable parameters may be provided to alter the amount of data scrubbed and how often the scrubbing of the data and determination of an updated AWP value occurs.

Next, step 206 is invoked to determine if there has been a recent price change to a manufacturer set price such as an AWP price change (e.g., typically the change in the manufacturer set price is a price increase). The detection of the AWP price change (or "new" AWP) may occur in a variety of different ways. The system may receive updated AWP information on various drugs (or other items associated with a particular AWP) from manufacturers directly (as the manufacturers drive AWP price updates) or monitoring services. For example, the services of First Databank, Inc. may be utilized to monitor AWP price updates. The period of time considered to be a "recent" price change may be any set length of time, or may be as long as the AWP price change remains unrecognized by one or more payers.

For all reimbursement claims where there is an AWP price change detected from the manufacturer or a monitoring service, etc., step 208 is invoked to store the reimbursement claim information in a transaction table located in one or more databases associated with the AWP module. If no AWP price change is detected, then storing the submitted claim information is not necessary (though may be done for reporting or system monitoring purposes) and the AWP monitoring process may be exited.

Once an updated AWP value has been detected, step 210 is invoked to monitor adjudicated claims, by a particular payer, and determine when the payer adjudicating submitted claims has updated their records to reflect the recent change in the AWP price established by the manufacturer. In step 210, a series of calculations may be conducted to determine if a claim was paid using an old AWP value (rather than the AWP value updated by the manufacturer) and should be presented to the customer as a resubmission opportunity. In an exemplary embodiment of the invention, determining a change in an AWP value for a particular payer is done by reviewing the reimbursement values associated with recently adjudicated reimbursement claims submitted to that particular payer and comparing them to older reimbursement values adjudicated by the same payer, to determine when the payer (or payers) have updated its internal pricing values (e.g., internally stored AWP values) to reflect the new global price associated with the drug set by the manufacturer(s). This determination may be used to identify the specific date/time the "new" AWP set by the manufacturer has been recognized and/or implemented by that particular payer. Typically, a payer's reimbursement value is the AWP minus a percentage of the AWP (e.g., AWP-%, other factors and values may be included in a reimbursement calculation, such as a patient's co-pay, etc., but for purposes of simplicity such factors are not discussed herein, though appreciable by one of ordinary skill in the art). For example, if the AWP is $100 and the reimbursement of the claim was for $50, then the payer reimburses for the AWP value minus 50%.

An exemplary calculation to determine when a particular payer has updated their internal AWP value used for adjudicating claims may be where a reimbursement claim for drug A is $50 and the AWP is $100 (e.g., the payer is only reimbursing $50 of the AWP established by the manufacturer). However, the manufacturer increases the AWP to $120—a 20% increase. The system then monitors claims for that same drug adjudicated by that same payer until the reimbursement value reflects approximately the same percentage increase associated with the "new" AWP set by the manufacturer(s). In other words, for this example, the adjudicated claims associated with the same drug are monitored until the reimbursement value is approximately $60 (a 20% increase over the previous reimbursement value of $50). At that time, the system determines that the payer has updated their internal AWP value to reflect the "new" AWP price set by the manufacturer.

Once the system detects that the payer's internal pricing has been updated, further calculation may be conducted to determine the actual percentage of change in the internal AWP price utilized by the payer for reimbursing claims (the new internal AWP price utilized by the payer may also be extracted from such a calculation). In alternative embodiments of the invention, other calculations and processes used to determine when a payer updates its internal AWP values used to adjudicate claims for reimbursements may also be implemented. In other embodiments the set time when a particular payer updates its AWP values used to adjudicate claims may be known. In such a case, the determination of when a payer's AWP values have been updated through the comparison of recently adjudicated claims to older previously submitted claims or various other calculations may not be necessary. Such information may also be useful when the manufacturer decreases the AWP associated with a particular drug and the payer may not have updated their internal AWP value yet.

When a new AWP has been detected as well as confirmed that the payer to which the claim was submitted is now honoring the new AWP, the customer may then be notified that the payer now honors the updated AWP value, which may be utilized for customer claim reversals, claim resubmissions, or future reimbursement claims. Opportunities for claim reversal/resubmission or a report notifying a customer of potential claim reversal or resubmission opportunities may be presented to a customer in a variety of ways selected by the customer (e.g., pharmacy) and determined in step 212. Two of those presentment means are mentioned in the exemplary embodiment of FIG. 2 and described in further detail in FIGS. 3-5. The first is invoked in step 214, where a customer is provided with a report, which will enable the customer to perform the actual reversal and resubmission from their system. Such a report may be provided to a customer at a period time interval that may be established by the customer or whenever a customer requests such a report. The second form of presentment for claim reversal or resubmission is an online resubmission invoked by step 216, where the customer is provided with a web-enabled user interface to approve some or all transactions for reversal and resubmission back through the host server and AWP module.

With regard to the option where a customer is provided with a report, an exemplary report 302 is shown in FIG. 3. Once it has been determined that the payer has updated the AWP pricing in their system and the customer elected the "report only" option (e.g., any reversal/resubmission of a reimbursement claim will occur at the customer level), a report 302 will be generated and available to the customer via email link or user interface to a reporter system. Customers will be able to use the information listed in the report 302 to determine if they wish to resubmit a transaction through their system. FIG. 3 shows an exemplary report 302 generated to summarize a customer's reversal/resubmission opportunities according to one embodiment of the present invention. As shown in the AWP Resubmission Report 302 of FIG. 3, the customers will be able to use the following information to determine if they wish to resubmit a transaction through their system: Store ID (or National Association of Boards of Pharmacy "NABP" identification number), Rx number, fill date, AWP effective date, BEN, BIN Description, NDC, drug name, old AWP (per unit), new AWP (per unit), original ingredient cost paid (along with its percentage off of the new AWP and percentage off the old AWP), potential opportunity (e.g., monetary amount that may be received if a resubmission is successful), opportunity date (e.g., date the payer updated its internal AWP), etc. Other information such as quantity of prescription, Pharmacy Care Network "PCN" number, amount the patient paid (e.g., co-pay), or Group ID may also be included in the report 302. The amount of transactions displayed may also be varied depending on the date range associated with the report 302.

The information shown in the report 302 of FIG. 3 is similar to that of the transaction file described with reference to FIG. 5 below, except that the transaction file of FIG. 5 includes information about reversal and/or resubmission claims that were accepted, rejected, as well as the details of those transactions. In contrast, the generated report 302 shown in FIG. 3 only provides information relating to claim submissions that have the potential to be reversed and/or resubmitted and the customer handles the creation of the reversal and/or resubmission claims themselves.

The second form of presentment for claim reversal or resubmission is an online resubmission option, where the customer is provided with a web-enabled user interface to approve some or all transactions for reversal and resubmission. This will be discussed in further detail with reference to FIG. 5 below. In an exemplary embodiment of the invention a transaction file may be accessible via the user interface or otherwise presented to a customer (e.g., email, FTP, fax, etc.) to allow the customer to update their pharmacy and accounts receivable system. The user interface may be accessible through a web browser and require a log-in with password or other security features appreciable by one of ordinary skill in the art. In an alternative embodiment of the invention, the customer may provide instructions for the automatic submission of a reversal claim and/or resubmission claim (without requiring customer interaction through the user interface to initiate the resubmission of a claim) upon the detection of an increase in the acceptable AWP value associated with a reimbursement claim.

FIG. 4 shows an exemplary user interface screen 402 offering user options to initiate claim reversal and resubmission according to one embodiment of the present invention. In the exemplary embodiment of the invention shown in FIG. 4, if the customer elects online resubmission the following actions 404 may be displayed to the customer through the user interface 402: "rebill," "remove," "pend," "add NDC to exclusion list," "download," etc. When the rebill option is selected a reversal of the original claim submission may be generated and the claim may then be resubmitted to realize the new AWP value now recognized by the payer. When the remove option is selected a transaction listed in the file is deleted. When "pend" is selected the listed transaction is placed on hold (or saved) for future processing. When "add NDC to exclusion list" is selected, the scrubbing routine is updated to detect future transactions associated with the same NDC and exclude them from being reported as potential reversal/resubmission candidates. When "download" is selected, information relevant to the transactions is downloaded to a memory location accessible from a computer. The downloaded information may be in the form of a transaction file, discussed with reference to FIG. 5 below. The customer may also sort transactions according to a variety of attributes 406 associated with the transaction including Store ID (NABP identification number), Prescription (Rx) number, fill date, AWP effective date, BIN, BIN Description, PCN number, percentage the original paid cost is off of the old AWP, the percentage the original paid cost is off of the new AWP, potential opportunity (e.g., monetary amount that may be received if a resubmission is successful), original ingredient cost paid, amount the patient paid (e.g., co-pay), NDC number, drug name, quantity (QTY) dispensed, etc. Other information such as old AWP (per unit), new AWP (per unit), opportunity date (e.g., suggested date a resubmission should be submitted) or Group ID, etc. may also be included in the user interface "Current View" screen 402.

As mentioned above with reference to the rebill option, the screen 402 shown in FIG. 4 allows the user to select the transactions the user would like to reverse and/or resubmit by checking the box 408 corresponding to the original transaction the user would like to have "rebilled." Other methods of selecting transactions through a user interface may be appreciable by one of ordinary skill in the art. When the customer indicates an authorization to resubmit the transaction(s) (e.g., selects a box 408 and selects the rebill option), the original claim submission is reversed. If the reversal is rejected by the payer, then the rejection is captured for reporting to the customer in a transaction file, discussed below in reference to FIG. 5, and a resubmission transaction is not made. If the reversal is accepted by the payer, then the claim is resubmitted. In the exemplary embodiment of the invention, all original claim information will remain the same.

For the online resubmission and/or reversal option selected to a customer, a transaction file may be generated that the customer may use to see the results of the resubmission and/or reversal process. Upon receipt of the adjudicated response of a resubmission or reversal claim (discussed above with reference to FIG. 4), a transaction file may be created and delivered to the customer. The transaction file may be delivered via email, fax, FTP or other communication means and may be a file configured for printing, or configured to appear in a particular format (e.g., Excel spreadsheet), or may be posted "on-line" as part of webpage accessible via a user interface. The transaction file may also be downloaded from the website through the user interface.

In an exemplary embodiment of the invention, the file may be delivered by emailing a URL link to the AWP Report system, download reports from the user interface, FTP, or other means of electronic communication. The specific data reported in an exemplary transaction file is discussed in detail with reference to FIG. 5. FIG. 5 shows an exemplary "Activity Summary" screen 502, which displays information stored in a transaction file, accessed through the user interface summarizing resubmitted (or reversed) claim transactions according to one embodiment of the present invention. In exemplary embodiments of the invention, these transaction files may be generated as the resubmission or reversal claims are being processed, at period intervals, or at the customer's request. In an exemplary embodiment of the invention, the transaction files may be generated nightly for each customer who selected transactions for resubmission or reversal during the past 24 hours. If there were no resubmissions or reversals selected to be processed during the previous time interval, a transaction file does not need to be generated. Other time intervals (weekly, monthly, at the customer's request, etc.) for claim resubmission and/or reversal monitoring and transaction file generation may also be used.

As shown in the screen 502 of FIG. 5, the transaction file may include the date of service, the Rx Number (prescription number from a resubmission), Store ID (or NABP or National Council for Prescription Drug Programs, Inc. "NCPDP" provider ID number), the date/time stamp when the reversal or resubmitted claim was processed, status of the reversal (e.g., 'A' for "accepted," though other indications may be provided in alternative embodiments), status of billing (e.g., 'P' for "paid" and 'C' for "captured," though other indications may be provided in alternative embodiments), routing BIN, NDC number of the resubmission and/or reversal, the drug name (e.g., a text description of the NDC number from the FDB file may also be included), the original ingredient cost paid, the submitted AWP associated with the resubmitted transaction, the new ingredient cost paid from the adjudicated response, and the increased reimbursement value (e.g., the payer ingredient cost paid—the original ingredient cost paid). Additionally, rejection codes may be provided to indicate a rejection of a reversal and/or a resubmission as well as an indication of the reason for the rejection from the payer (e.g., included with the adjudicated response). The transaction file may also be sorted or reorganized in ascending or descending order based on the various attributes 504 presented on the screen. The amount of transactions displayed may also be varied depending on the date ranges selected.

As shown in the summary 506 of the "Activity Summary" screen of FIG. 5, various calculations and statistical information may be included in a transaction file such as: a count of all reversals and/or resubmissions included in the file, the sum of the increased reimbursements, the total number of reversal and/or resubmission rejections, the percentage of rejections (e.g., total rejections divided by total claims), resubmission rejections originally paid, etc. Other information may be included in the transaction file, such as detailed descriptions of a reason for a rejection, percent of successful reimbursement resubmissions, running total on increased reimbursements for the customer; percentage increase in an increased reimbursement, or other data relating to a reversal or resubmission of a claim that the customer may find useful for monitoring, accounting (e.g., accounts receivable and/or cash flow), auditing, etc.

Accordingly, many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of this application. Although specific terms are employed herein, they are used in a generic and descriptive sense only and not for purposes of limitation.

The invention claimed is:

1. A method, comprising:
monitoring, by a host server, a plurality of adjudicated claims received from a payer system, wherein at least one of the plurality of adjudicated claims received from the payer system is associated with a drug;
determining, by the host server, that the payer system has updated an internal pricing value associated with the drug; and
generating notification that the payer system has updated the internal pricing value associated with the drug.

2. The method of claim 1, further comprising:
receiving an indication of a change in a price associated with the drug, wherein the indication of the change in the price associated with the drug is received from a third party entity.

3. The method of claim 2, wherein the received indication of the change in the price associated with the drug comprises an indication of a change in a manufacturer set price associated with the drug.

4. The method of claim 2, wherein the received indication of the change in the price associated with the drug comprises an indication of a change in one of an Average Wholesale Price (AWP) associated with the drug, a Wholesale Acquisition Cost (WAC) associated with the drug, or a Maximum Allowable Cost (MAC) associated with the drug.

5. The method of claim 1, further comprising:
receiving an indication of a change in a price associated with the drug, wherein the price associated with drug is set by a government agency.

6. The method of claim 1, wherein generating the notification that the payer system has updated an internal pricing value associated with the drug includes generating a report, wherein the report includes a potential reimbursement value associated with the drug based on the determination of an updated internal pricing value associated with the drug.

7. The method of claim 6, further comprising:
determining at least one of the plurality of adjudicated claims received from the payer system is to be excluded from the report.

8. The method of claim 7, wherein the determining at least one of the plurality of adjudicated claims received from the payer system is to be excluded from the report includes excluding the at least one of the plurality of adjudicated claims received from the payer system based at least in part on (1) the Bank Identification Number (BIN) or National Drug Code (NDC) associated with the at least one of the plurality of adjudicated claims, (2) the at least one of the plurality of adjudicated claims was paid at the Usual and Customary (U&C) rate, (3) the at least one of the plurality of adjudicated claims was a same-day or prior-day reversal transaction, or (4) the at least one of the plurality of adjudicated claims was a 100% co-pay claim.

9. The method of claim 7, wherein determining at least one of the plurality of adjudicated claims received from the payer system is to be excluded from the report includes excluding the at least one of the plurality of adjudicated claims received from the payer system based at least in part on the at least one of the plurality of adjudicated claims being associated with an amount of change in a reimbursement value that does not meet a threshold value.

10. The method of claim 6, wherein the report is accessible via a web browser.

11. The method of claim 1, wherein generating the notification that the payer system has updated an internal pricing value associated with the drug includes providing access to claim information through a user interface.

12. The method of claim 1, wherein determining that the payer system has updated an internal pricing value associated with the drug includes:
reviewing a first reimbursement value associated with a first adjudicated reimbursement claim adjudicated by the payer system; and
comparing the first reimbursement value to a second reimbursement value associated with a second adjudicated claim adjudicated by the payer system.

13. The method of claim 1, further comprising:
determining if the payer system has updated an internal pricing value associated with the drug;
upon receiving a request from a user, creating a reversal transaction of at least one adjudicated claim associated with the drug; and
submitting the reversal transaction to the payer system.

14. The method of claim 13, further comprising:
upon acceptance of the reversal transaction by the payer system, automatically resubmitting the at least one adjudicated claim.

15. The method of claim 14, further comprising:
creating a transaction file, wherein the transaction file includes a plurality of attributes associated with the resubmitted at least one adjudicated claim.

16. The method of claim 15, further comprising:
providing access to the transaction file through a user interface.

17. The method of claim 16, wherein the transaction file is sortable based on at least one of the plurality of attributes associated with the resubmitted at least one adjudicated claim.

18. The method of claim 15, further comprising:
transmitting the transaction file to a user.

19. A system for reimbursing prescription fulfillment comprising:
a database, wherein the database includes computer executable instructions;
a processor, in communication with the database, wherein the processor executes the computer executable instructions to:
monitor a plurality of adjudicated claims received from a payer system, wherein at least one of the plurality of adjudicated claims received from the payer system is associated with a drug;
determine that the payer system has updated an internal pricing value associated with the drug; and
generate notification that the payer system has updated the internal pricing value associated with the drug.

20. The system of claim 19, wherein the processor is further configured to execute computer executable instructions to:
receive an indication of a change in a price associated with the drug, wherein the indication of the change in the price associated with the drug is received from a third party entity.

21. The system of claim 20, wherein the received indication of the change in the price associated with the drug comprises an indication of a change in a manufacturer set price associated with the drug.

22. The system of claim 20, wherein the received indication of the change in the price associated with the drug comprises an indication of a change in one of an Average Wholesale Price (AWP) associated with the drug, a Wholesale Acquisition Cost (WAC) associated with the drug, or a Maximum Allowable Cost (MAC) associated with the drug.

23. The system of claim 19, wherein the processor is further configured to execute computer executable instructions to:
receive an indication of a change in a price associated with the drug, wherein the price associated with the drug is set by a government agency.

24. The system of claim 19, wherein the computer executable instructions to generate notification that the payer system has updated an internal pricing value associated with the drug include computer executable instructions to generate a report, wherein the report includes a potential reimbursement value associated with the drug based on the determination of an updated internal pricing value associated with the drug.

25. The system of claim 24, wherein the processor is further configured to execute the computer executable instructions to:
determine at least one of the plurality of adjudicated claims received from the payer system is to be excluded from the report.

26. The system of claim 25, wherein the computer executable instructions to determine at least one of the plurality of adjudicated claims received from the payer system is to be excluded from the report include computer executable instructions to exclude the at least one of the plurality of adjudicated claims received from the payer system based at least in part on (1) the Bank Identification Number (BIN) or National Drug Code (NDC) associated with the at least one of the plurality of adjudicated claims, (2) the at least one of the plurality of adjudicated claims was paid at the Usual and Customary (U&C) rate, (3) the at least one of the plurality of adjudicated claims was a same-day or prior-day reversal transaction, or (4) the at least one of the plurality of adjudicated claims was a 100% co-pay claim.

27. The system of claim 25, wherein the computer executable instructions to determine at least one of the plurality of adjudicated claims received from the payer system is to be excluded from the report include computer executable instructions to exclude the at least one of the plurality of adjudicated claims received from the payer system based at least in part on the at least one of the plurality of adjudicated claims being associated with an amount of change in a reimbursement value that does not meet a threshold value.

28. The system of claim 24, wherein the report is accessible via a web browser.

29. The system of claim 19, wherein the computer executable instructions to generate notification that the payer system has updated an internal pricing value associated with the drug include computer executable instructions to provide access to claim information through a user interface.

30. The system of claim 19, wherein the computer executable instructions to determine that the payer system has updated an internal pricing value associated with the drug include computer executable instructions to:
review a first reimbursement value associated with a first adjudicated reimbursement claim adjudicated by the payer system; and
compare the first reimbursement value to a second reimbursement value associated with a second adjudicated claim adjudicated by the payer system.

31. The system of claim 19, wherein the processor is further configured to execute the computer executable instructions to:
determine if the payer system has updated an internal pricing value associated with the drug;
upon receiving a request from a user, create a reversal transaction of at least one adjudicated claim associated with the drug; and
submit the reversal transaction to the payer system.

32. The system of claim 31, wherein the processor is further configured to execute the computer executable instructions to:
upon acceptance of the reversal transaction by the payer system, automatically resubmitting the at least one adjudicated claim.

33. The system of claim 32, wherein the processor is further configured to execute the computer executable instructions to: create a transaction file, wherein the transaction file includes a plurality of attributes associated with the resubmitted at least one adjudicated claim.

34. The system of claim 33, wherein the processor is further configured to execute the computer executable instructions to: provide access to the transaction file through a user interface.

35. The system of claim 34, wherein the transaction file is sortable based on at least one of the plurality of attributes associated with the resubmitted at least one adjudicated claim.

36. The system of claim 33, wherein the processor is further configured to execute the computer executable instructions to: transmit the transaction file to a user.

37. A computer readable medium having stored thereon computer executable instructions for performing a method comprising:
monitoring a plurality of adjudicated claims received from a payer system, wherein at least one of the plurality of adjudicated claims received from the payer system is associated with a drug;
determining that the payer system has updated an internal pricing value associated with the drug; and
generating notification that the payer system has updated the internal pricing value associated with the drug.

* * * * *